United States Patent
Couderc et al.

(10) Patent No.: US 10,085,667 B2
(45) Date of Patent: Oct. 2, 2018

(54) ECG CLOCK ELECTROCARDIOGRAM BASED DIAGNOSTIC DEVICE AND METHOD

(71) Applicant: University of Rochester, Rochester, NY (US)

(72) Inventors: Jean-Philippe Yves Couderc, Rochester, NY (US); Mehmet Kemal Aktas, Penfield, NY (US); Tolga Soyata, Pittsford, NY (US); Alex Tyndall Page, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 15/368,587

(22) Filed: Dec. 3, 2016

(65) Prior Publication Data

US 2017/0156619 A1 Jun. 8, 2017

Related U.S. Application Data

(60) Provisional application No. 62/263,234, filed on Dec. 4, 2015.

(51) Int. Cl.
*A61B 5/0452* (2006.01)
*A61B 5/044* (2006.01)
*A61B 5/04* (2006.01)
*A61B 5/00* (2006.01)
*A61B 5/0245* (2006.01)

(52) U.S. Cl.
CPC .......... *A61B 5/0452* (2013.01); *A61B 5/0006* (2013.01); *A61B 5/0245* (2013.01); *A61B 5/044* (2013.01); *A61B 5/04017* (2013.01); *A61B 5/7203* (2013.01)

(58) Field of Classification Search
CPC ... A61B 5/0452; A61B 5/0006; A61B 5/0245; A61B 5/04017; A61B 5/044; A61B 5/7203
See application file for complete search history.

(56) References Cited

U.S. PATENT DOCUMENTS

| | | | |
|---|---|---|---|
| 2011/0125042 A1* | 5/2011 | Xue | A61B 5/044 600/523 |
| 2014/0073486 A1* | 3/2014 | Ahmed | A61B 5/02405 482/9 |

* cited by examiner

*Primary Examiner* — Joseph Dietrich
(74) *Attorney, Agent, or Firm* — Patent Technologies, LLC; Robert D. Gunderman, Jr.

(57) ABSTRACT

An ECG clock electrocardiogram based diagnostic device and method is disclosed. The ECG clock provides a clear visual indicator of heart related anomalies such as Long QT syndrome over a longer span of time than can otherwise be assimilated by a medical practitioner. A variable such as QT interval is represented by a variable length radial hand similar to a watch or clock hand. The circular face of the ECG clock represents the diagnostic time interval, typically 24 hours. The resulting output or plot of the ECG clock portrays a circular or polar mapping of the heart related variable such as QT interval over the diagnostic time interval, facilitating rapid diagnosis of volumes of electrocardiogram data by a medical practitioner that has heretofore not been possible.

20 Claims, 8 Drawing Sheets
(7 of 8 Drawing Sheet(s) Filed in Color)

ECG CLOCK ELECTROCARDIOGRAM BASED DIAGNOSTIC DEVICE AND METHOD

CROSS REFERENCE TO RELATED PATENT APPLICATIONS

This application claims priority to U.S. Patent Application Ser. No. 62/263,234 filed Dec. 4, 2015 entitled "ECG Clock Electrocardiogram Based Diagnostic Device And Method" by Coudere et al., the entire disclosure of which is incorporated herein by reference.

STATEMENT REGARDING FEDERALLY SPONSORED RESEARCH OR DEVELOPMENT

This invention was made with Government Support under Contract #HL096556, HL114944 awarded by National Institutes of Health and CNS-1239423 awarded by the National Science Foundation. The government has certain rights in the invention.

BACKGROUND OF THE INVENTION

1. Field of the Invention

The present invention relates generally to cardiology, and more particularly to an ECG clock electrocardiogram based diagnostic device and method.

2. Description of the Related Art

Holter monitors are portable electrocardiogram (ECG or EKG) recorders used for long-term patient monitoring. They are incredibly valuable tools, as many cardiac events of interest to medical practitioners will not occur during brief recordings in a clinic. Instead, the patient must be monitored throughout their normal daily activities. After recording a patient for some time, usually 24 hours, data that has been collected by the Holter monitor is extracted and analyzed. A physician is then presented with a summary of events that occurred during the Holter recording such as min., max., and average values for a handful of important parameters like heart rate, for example. If a dangerous value is detected at some point in the recording, or the patient indicates that a symptom was experienced at a certain time of day, the physician might investigate further by manually checking the electrocardiogram tracing collected by the Holter monitor at the time of the event. This process is somewhat tedious, particularly if the physician has many patients to monitor. Additionally, the recording summaries that are presented to the physician may drastically over-simplify the results, preventing the physician from uncovering relevant and important information. Therefore, there is a clinical need for a system that presents 24-hour electrocardiogram data in a simple form that is easy to read and interpret without over-summarizing it. Such a system would be extremely useful for diagnosis and monitoring of heart disease and anomalies.

An example of a heart anomaly that would benefit from such a system is Long QT Syndrome. Long QT Syndrome causes ventricular arrhythmia (and often, death) in thousands of people in the US each year. The risks associated with this congenital disease can be mitigated somewhat through medication and lifestyle changes. Specific genotype and other factors make the risk for fatal events highly individualized, so long-term monitoring is crucial in prescribing the best possible treatment. The advent of portable medical sensors including electrocardiograms (ECGs) makes long-term remote monitoring much more convenient for both doctor and patient. The collection of large amounts of ECG data is also incredibly valuable to researchers, for identifying trends and developing decision support algorithms, for example. However, analyzing the vast amounts of data obtained from these sensors represents a serious challenge. In a typical day the human heart beats approximately 100,000 times, and a physician would like to observe the patient over a diverse set of activities that span very differing timeframes (for example, from sleep and exercise down to events that may last only a few minutes). What is therefore needed is a system and method for visualizing electrocardiogram data that may span 24 hours or more, providing the physician with a diagnostic tool that has heretofore not existed.

BRIEF SUMMARY OF THE INVENTION

In accordance with the present invention, there is provided an ECG clock electrocardiogram based diagnostic device comprising a means for receiving electrocardiogram data wherein the electrocardiogram data comprises an ECG variable such as $QT_c$ interval values and a time of day value associated with each ECG variable; a clock for display on, for example, a computer display, comprising a variable length radial hand and a circular face wherein a complete 360 degree rotation of the variable length radial hand correlates to a diagnostic time interval and wherein the length of the radial hand at a given angular position on the circular face correlates to an ECG variable value that is unique to the time of day associated with that angular position.

The ECG clock may be used for novel diagnostic methods such as determining stimuli that influence an ECG variable such as $QT_c$ interval values and taking actions to correct or modify those stimuli in order to bring the ECG variable into a safe range. The ECG clock provides an instrument or visual representation of the change in ECG value with a change in stimulus or event. The actions that may be taken to correct or modify the stimuli or event that resulted in the change in ECG variable may include, for example, adapting or modifying pharmacological treatment. Other actions may include physiological actions such as modification of sleeping patterns, eating patterns, exercise regimen, and the like. The ECG clock may also be used for novel analytical and research methods where ECG data from a given research group or groups is used in an ECG clock or clocks so that conclusions can be drawn for that group, and courses of action taken or defined. Novel methods of the ECG clock may also include display of the ECG clock on a computer, smart phone, tablet or flat panel screen, display of the ECG clock on a wrist worn computing device, or the like. Other novel methods of the ECG clock include providing the data for the ECG clock, in either numerical or graphical format, to another system such as a downstream or upstream computer system or the like. Further methods may include patient monitoring, tracking of drug therapy outcome, adjustment of therapy based on ECG clock display, and the like. The ECG clock display may, in some embodiments of the present invention, be color coded to provide a visual indication of safe and unsafe ECG parameters being displayed.

The foregoing has been provided by way of introduction, and is not intended to limit the scope of the invention as described by this specification, claims, and the attached drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will be described by reference to the following drawings, in which like numerals refer to like elements, and in which.

Figure 1:
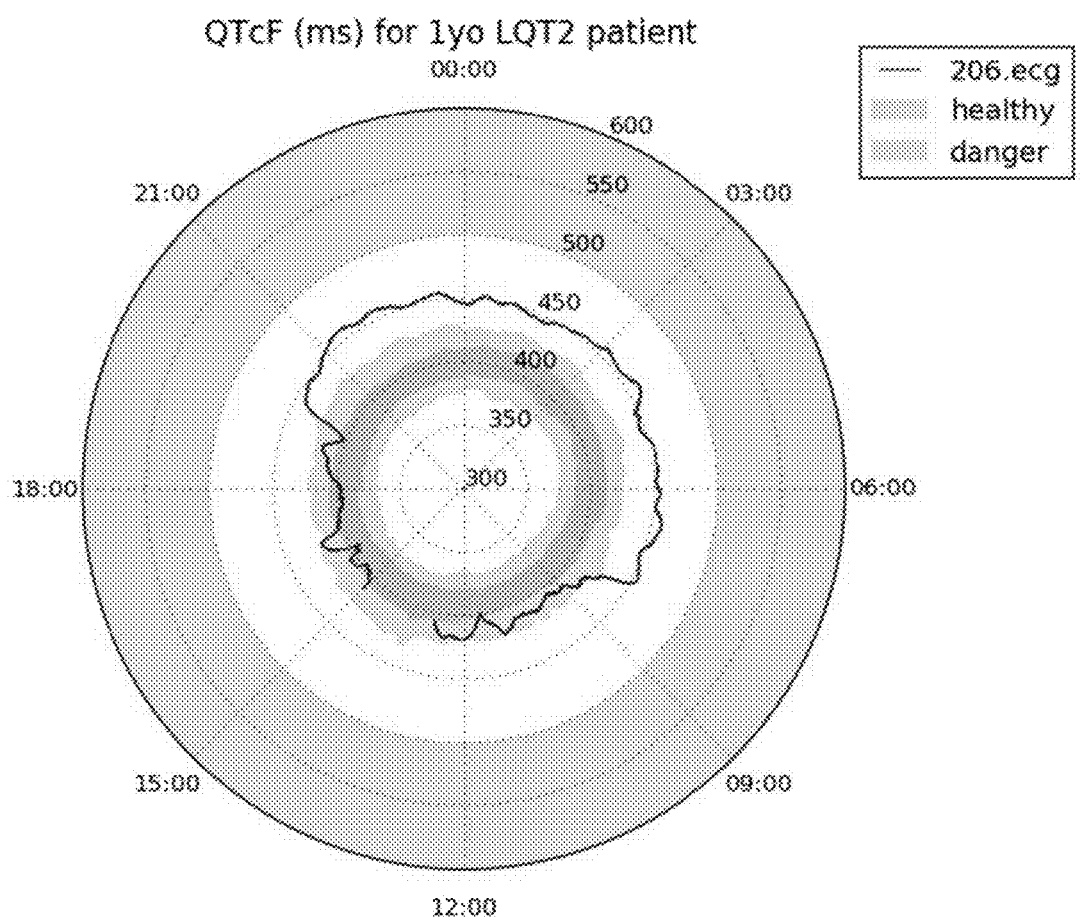
FIG. 1 depicts an example of an ECG clock of the present invention.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims, and drawings attached hereto.

DESCRIPTION OF THE PREFERRED EMBODIMENTS

The ECG clock electrocardiogram based diagnostic device, system and methods described herein allows for the review of a large set of electrocardiogram measurements (such as the QTc interval) while providing a visual, graphical and "infographic" understanding of single and/or multiple days of measurements. The electrocardiogram data may be received from, for example, a Holter monitor. The ECG clock is a circular plot representing a 24-hour watch (00:00 to 24:00) with midnight at the top of the clock. Of course other orientations and time intervals are to be considered as embodiments of the present invention as described and envisioned herein. The radius of the clock varies based on the electrocardiogram data for each time of day value and represents an ECG variable such as QTc interval values that vary from 0.3 seconds to 0.6 seconds from the center to the perimeter of the clock face. The clock is used to present information for multiple purposes and can be calibrated precisely to quickly identify abnormalities from the norm.

The QT interval is a measure of the time between the start of the Q wave and the end of the T wave in the heart's electrical cycle, representing the electrical depolarization and repolarization of the ventricles and corresponds to the time it takes for your heart to contract and then refill with blood before beginning its next contraction.

The ECG clock electrocardiogram diagnostic device comprises a means for receiving electrocardiogram data. The source of electrocardiogram data may be, for example, a Holter monitor. Data transfer may take place using any data transfer protocol, either wired or wireless. Data transfer may also take place by way of removable physical media such as solid state, magnetic, or optical memory. The electrocardiogram data may comprise, for example, $QT_c$ interval values and a time of day value associated with each $QT_c$ interval value. The clock itself comprises a variable length radial hand and a circular face wherein a complete 360 degree rotation of the variable length radial hand correlates to a diagnostic time interval (such as a 24 hour interval). The length of the radial hand at a given angular position on the circular face correlates to an ECG variable such as a $QT_c$ interval value that is unique to the time of day value associated with that angular position. As seen in the examples of the ECG clock provided in the drawings, with a plurality of data points the variable length radial hand is not necessarily visible. Instead, the radial hand sweeps a pattern on the circular or polar coordinate system that is considered to be the circular face of the ECG clock. Such a pattern may be in the form of an outline or a tracing, or may, in some embodiments of the present invention, be in the form of color coded banding or other geometric or graphical form. Thus, the variable length radial hand "paints" a geometric pattern or may trace a form that can be easily viewed and interpreted by a medical practitioner as part of a diagnostic method.

Further, in some embodiments of the present invention, a 3D or virtual three dimensional display of the electrocardiogram clock may be employed. Such a three dimensional representation would allow for "stacked" clock displays, for example, a stack of clock displays where each layer represents a time interval such as a day and the entire three dimensional model represents a month in totality, where the practitioner is able to slice the three dimensional model on the computer screen to access an individual day (or other time interval). In this way, patterns that may encompass day of week or time of day may be more easily spotted. Appropriate three dimensional viewing tools may also be employed to facilitate display on an appropriate computer display.

The ECG clock can be used for many diagnostic and clinical applications such as:

1.) Viewing the dynamic and beat-to-beat variations in QTc throughout a period of time.

2.) Detecting long term QTc deviations from the norm or baseline due to stressors such as lack of sleep, emotional distress, hormonal changes, mental/psychiatric disorders, fatigue, renal dysfunction, electrolyte abnormalities, physical activities, and others.

3.) Evaluating the efficacy and safety of approved and novel drug therapies and their impact on QTc measured in a continuous fashion and over a long period of time. The ECG clock may be used for safety surveillance in patients that have been prescribed with known QT-prolonging drugs, and when abnormalities are detected. Automatic color coded warnings (Red: QTc>500 msec, Yellow: QTc 460-500 msec. Green: QTc within normal range. Blue: QTc<320 msec) can be delivered to the patient and healthcare providers monitoring the patient.

4.) Monitoring of patients (both inpatient and outpatient) with arrhythmias such as atrial fibrillation who are started on QT prolonging drugs like class III antiarrhythmics such as dofetilide, sotalol, amiodarone, ibutilide. The ECG clock can be used to generate patient specific automatic alerts to the patient and/or healthcare provider indicating the need for interventions such as drug dose adjustments, and/or to verify medication adherence.

5.) Gathering and displaying continuous and long-term retrospective as well as prospective inputs which can be analyzed to predict response to therapy and understand QT dynamics and its impact on clinical outcomes such as syncope, ventricular arrhythmias and sudden death. These and other research applications for the ECG clock will become further evident upon reading this specification.

6.) Decision making, diagnostics and confirmation of diagnostics. The ECG clock may be visually interpreted by a medical practitioner or an augmented version of the ECG clock may be interpreted by the medical practitioner, where augmentation may be performed by a machine such as a computer. Augmentation may include, but is not limited to, banding and color coding, comparison against known disease states, probability and statistical analysis, and the like.

The ECG clock of the present invention provides a great opportunity to study various cardiac features by hour, day of week, season, etc. Time and date can be extracted from Holter recordings, yet such analyses are rarely presented. With a feature like heart rate (HR), for example, the present invention provides much more than simply the mean or standard deviation in a given population; these statistics can be presented for every minute of the day, yielding more accurate reference values for clinical use. Further, by using the demographic information in the THEW (Telemetric and Hotter ECG Warehouse—www.thew-project.org) database, one is able to separate results by age, gender, the presence of beta blockers, and other factors. Our analysis of heart rate in 200 healthy subjects revealed interesting features in the daily cardiac cycle, such as the difference and transition of heart rate between night and day, and maxima and minima around meals. After our initial investigation of heart rate patterns in THEW recordings, we shifted our focus to another cardiac interval: QT. Prolongation of the QT interval can greatly increase the risk of ventricular fibrillation, so it is an important marker for cardiologists to monitor. During the course of our research, we developed the ECG clock as a method of visualizing QTc—the corrected QT interval—over 24-hour data sets. The ECG clock is a polar plot representing a 24-hour clock. The radius represents the value of the feature (QTc), and the angle is time of day. An example plot is given in FIG. 1. The recording is of a 1-year-old LQT2 female from the THEW E-HOL-03-0480-013 database. We see that she stays in the same QTc range as her healthy (i.e. no LQTS genotype) peers during the day, but has slightly prolonged QTc at night.

There are two particularly important features to note in FIG. 1:

(1) the blue line, representing the value of a single cardiac feature (QTc) for a specific patient, and (2) the green area, representing the range of normal values for that feature based on analysis of recordings from healthy subjects. This presentation has many uses in clinical and research areas, as we will further demonstrate herein. Further, this visualization technique will continue to become more relevant; mobile ECG sensors become more commonplace, which increases the availability of data sets for research, and will overwhelm physicians if the data cannot be condensed. The ECG Clock library can be adapted to monitor virtually any cardiac feature over 24 hours. This specification focuses mainly on QTc visualization, but we also present case studies involving heart rate.

Figure 2:
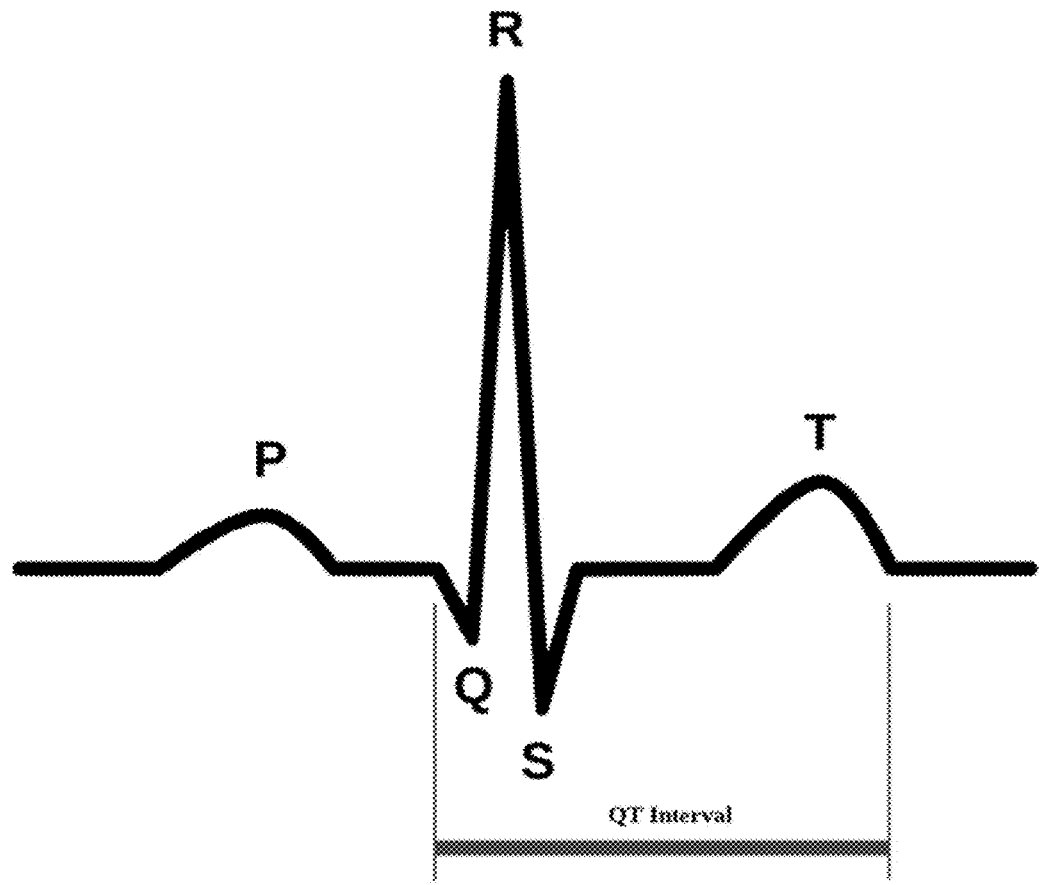
FIG. 2 is a graph of a typical ECG waveform for one cardiac cycle.

As previously stated, the QT interval is the time from the start of the Q wave to the end of the T wave in an electrocardiogram signal, and is depicted in FIG. 2. QTc is the "corrected" QT interval (based on heart rate), and is usually computed with one of the following two equations:

$$QTcB = QT/((RR/sec)^{(1/2)})$$

$$QTcF = QT/((RR/sec)^{(1/3)})$$

where the "B" and "F" indicate that these are the Bazett and Fridericia corrections, and the division by one second is to preserve the units of QT. The normal range of QTcB is roughly 356-449 msec. in men, and 369-460 msec. in women, according to Mason et al. in "Electrocardiographic Reference Ranges Derived From 79.743 ambulatory subjects", Journal of Electrocardiology, vol. 40, no. 3, pp. 228-234, 2007. QTc may be prolonged by drugs or genetic factors, and dangerous prolongation is known as the Long QT Syndrome (LQTS). When such prolongation occurs, subjects are prone to potentially-fatal arrhythmias like torsades de pointes (TdP). LQTS is responsible for an estimated 3000-4000 sudden deaths in children and young adults in the US each year according to G. M. Vincent M.D. in "The Molecular genetics of the long qt syndrome causing fainting and sudden death", Annual Review of Medicine, vol. 49, no. 1, pp. 263-274, 1998. At least thirteen genes have been identified that contribute to Long QT; LQT1 and LQT2 are the most common. FIG. 2 depicts a typical ECG waveform for one cardiac cycle, with key waves annotated. Prolongation of the QT interval relative to the total cardiac cycle can indicate a high risk for adverse events. (Image source: SinusRhythmLabels.png by Anthony Atkielski).

In at-risk patients, QT (and QTc) are typically computed from 10-second ECG snapshots during clinic hours. Or, if a Holter monitor is used, the physician is usually presented with very basic QT/QTc statistics such as min/max/mean. As mentioned previously, it is difficult or impossible to identify risky times of day for a given patient using only these checkup techniques. LQT2 patients, for example, are known to have more severe QTc prolongation at night, whereas LQT1 patients are more likely to experience symptoms during exercise, according to Schwartz et al. in "Genotype-phenotype correlation in the long-QT syndrome gene-specific triggers for life threatening arrhythmias", Circulation, vol. 103, no. 1, pp. 89-95, 2001. The "concealment" of LQTS in LQT2 patients during clinic hours poses one diagnostic challenge, and the varying penetrance of various LQTS genes poses another. To overcome these obstacles, we will characterize QTc across different populations/genotypes, and also plot QTc over 24-hour recordings. This presentation will allow identification of dangerous times or events, and will also be useful in drug trials and induction protocols.

Heart Rate Dipping

Elevated heart rate during sleep—i.e., failure of the heart rate to "dip" to a low enough level—has been associated with cardiovascular disease and an increased risk of all-cause mortality. Similarly, low heart rate variability (HRV) is an indicator of risk for cardiac event. A heart rate plot in the same style as FIG. 1 will provide insight into these two critical pieces of information.

Example of Data Preparation

In order to plot features like HR and QTc, we must first compute them. Holter recordings are generally not annotated with beat-to-beat interval values; they simply provide the raw ADC data (i.e. amplitude vs. time) for each ECG lead. We have access to hundreds of such recordings in the THEW database, and will extract the relevant values from them for our examples. To accomplish this, we use a library developed by Yuriy Chesnokov, as further described in "Individually Adaptable Automatic QT Detector" in Computers and Cardiology, 2006. IEEE, pp. 337-340, to annotate recordings from two primary THEW databases: Healthy (E-HOL-03-0202-003), and Genotyped LQTS (E-HOL-03-0480-013). The annotation library provides—among other things—the locations of Q onset, R. and T offset for every beat on each lead. We merge the annotations from all leads into a single list, keeping the median RR at each heart beat and the worst possible (i.e. longest) QT. QTc and HR are then computed from this consolidated data set. Noise/outliers are removed during plotting, as demonstrated herein. We will not be looking at any other features (such as PR or ST) in the examples provided herein, but the method of extracting them would be similar.

Statistics for Decision Support

As we saw in FIG. 1, it is helpful to compare a single patient to a larger population, e.g. to check where the patient's QTc falls relative to healthy subjects. We would therefore like the ECG Clock Library to be capable of loading reference ranges from disk, and adding them to the plot—i.e., we want to store the values used to generate the green range in the figure. Typical ranges for QTc (and other ECG parameters) have been thoroughly investigated, but reference ranges that take precise time of day into account do not exist. Because of the time-dependence of LQTS and heart rate dipping that we have already discussed, we have developed our own reference ranges from the THEW databases mentioned herein. The ECG Clock Library includes these ranges for many populations (separated by gender, LQT genotype, etc.), in CSV files with the following columns:

time of day|value ($0^{th}$ percentile)|value ($1^{st}$ percentile)| . . . |value ($100^{th}$ percentile)

Currently, we have only computed HR and QTc, however, other variables may be used and are considered to be a part of the present invention and the various embodiments described and envisioned herein. QTc values were pre-filtered with a sliding 10-minute median, but HR was not filtered because it is much easier to annotate and therefore less noisy. Use of these files is further described herein.

The ECG Clock Library

The ECG Clock library is written with the primary purpose of generating plots of ECG interval values on a 24-hour axis. There is a wide range of applications for such plots, some of which will be demonstrated herein.

System Requirements

The implementation of the ECG clock is described herein by example, and not limitation. As one skilled in the art will understand and appreciate, various hardware and software components may be used or interchanged without detracting from the spirit and broad scope of the present invention and the various embodiments described and envisioned herein.

In one embodiment of the present invention, to generate plots, we use Python and the well-known matplotlib library. Working in Python also allows us to parse input files very easily; the dateutil module is quite helpful in this process. The final module that is required (outside of the standard library) is numpy. The code has been tested in Python 2.7 and 3.4.

Input File Specifications

ECG annotations should be provided as CSV files. Ideally, the file will contain one {time, value} pair per row, but you may also choose to specify the column numbers to plot from a larger file. Time may be stored in relatively arbitrary strings, such as "11:16" or "2015-07-15T11:16:00.535". Values (e.g. QTc) should be stored in milliseconds, but the library will attempt to convert them from seconds if necessary. If this automatic conversion should not be applied to your data, you may choose to create a new subclass for your application, or comment/remove the sec_to_msec calls.

Although an unlimited number of recordings can be added to the same plot—to view a patient's response to different prescriptions, for example—we find that the plots tend to get cluttered with more than 3-4 recordings. Incorporation of additional information (e.g. from more sensors, which are not necessarily cardiac) on the same axes is an ongoing research challenge; we expect that plots of heart rate and QTc together, or QTc and TpTe, for example, will make it easier to gauge the interaction between related features and in some embodiments non-ECG features. We will likely implement these functions in the library as they become more relevant to our research.

Structure and Usage

The ECG Clock library has one main class, ECGClock, that provides most standard functions such as the ability to add a recording or an annotation to a polar axis, save the plot to a file, etc. For our analysis of QTc, we created a subclass called QTClock that adds features such as highlighting standard "dangerous" ranges specific to QTc. (If, for example, you intend to look at ST segment amplitude, perhaps you would subclass ECGClock as STClock and add functions that highlight areas of ST depression or elevation in different colors, as well as changing the default axes ranges in _init_.) Finally, there is an ECGFigure class which basically holds many ECGClock subplots. You may think of ECGFigure and ECGClock as behaving like the Figure and Axes objects in matplotlib, though they are not actually extensions of those classes. There are various ways to interface with the library. Two examples are:

1.) Importing it in another Python script. Using this method, the end user will likely need less than 10 lines of code to generate each of their plots. See clock_example.py in the Git repository for a demonstration, or the code in the later Figures.

2.) For simple ECG clocks, you may directly run QTClock.py from the command line. This method does not provide access to all features, but can be used to generate basic QTc plots in a single line. QTClock.py-h explains the syntax; an example would be:
QTClock.py-i qtcf_ann.csv-f 10-o output.png to plot the QTc values from qtcf_ann.csv} on a standard axis, with a 10 minute filter width, and save as output.png.

Basic Features

Output Options:

Plots may be saved to disk using the save( ) function, or displayed in an interactive window using show( ). File output is ideal for batch processing, whereas the interactive view is useful for measuring QTc at "interesting" times and/or adjusting the plot range before saving.

Ranges:

The red and green background highlights in FIG. 1 provide decision support for the clinician. The utility of the static red range is self-explanatory, and for ECG clocks, it can be added and customized using the add_danger_range( ) function. The green area displayed in the figure is more dynamic; we show the interquartile range (IQR) of QTc in healthy patients (using the stored ranges provided) in dark green, and a wider percentile range (5-95%) of QTc in those patients in lighter green. This provides a reference of what is normal/healthy. You may also elect to show a static range—350 ms to 450 ms, for example—rather than varying the values throughout the day. This is possible with the add_healthy_range( ) function. Or, instead of comparing a patient to the healthy group, you may wish to compare them to their peers with the same genotype. To do this, you may select, for example, LQT2 female.csv rather than healthy_female.csv" when calling add_percentile_range( ). Note that due to the relatively small number of recordings in the THEW databases, extreme percentile values (such as 99%)

are likely to reveal noise rather than accurate values at some times of day. For this reason, add_percentile_range( ) accepts a smoothing argument. With our data and annotation algorithm, roughly the 20-80 percentile range seems to provide a good reference.

Figure 3:
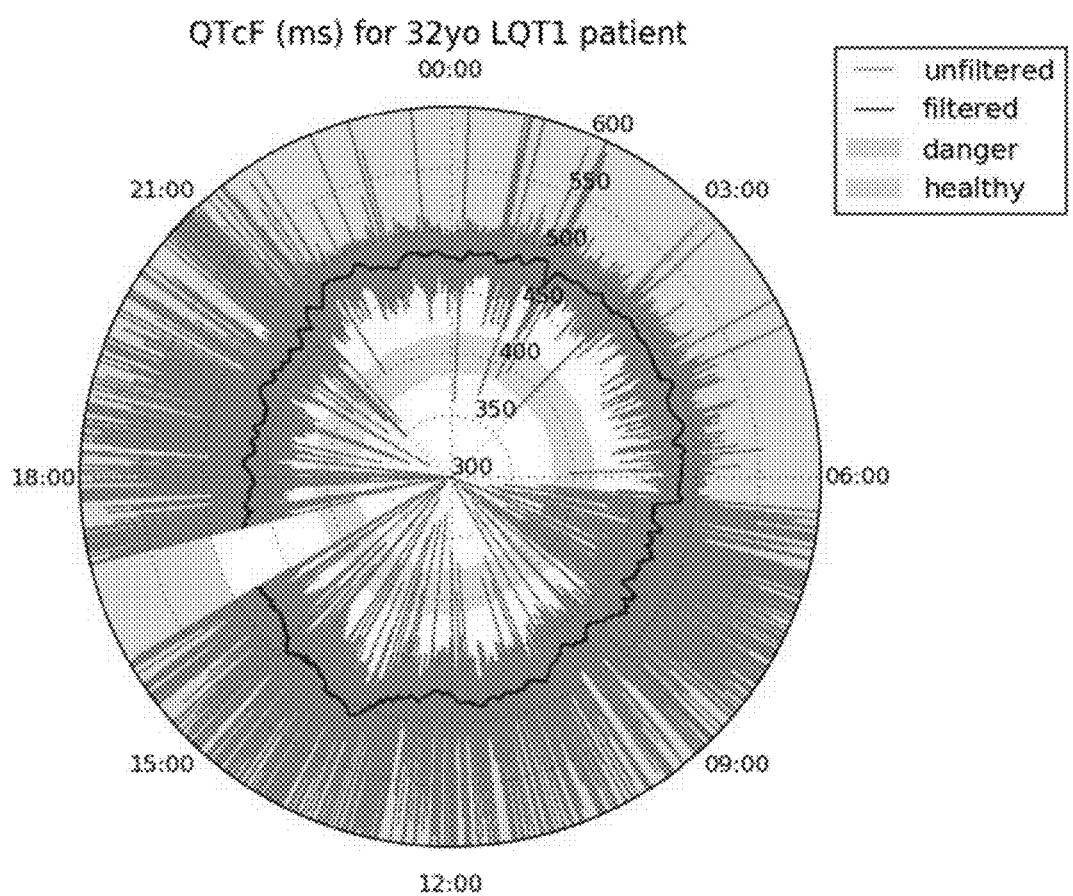
FIG. 3 is an ECG clock portraying filtering of noisy annotations.

Filtering:

Beat-to-beat annotations are often very noisy, requiring filtering to view. You do not need to pre-filter such data before opening it in the ECG Clock library; you may simply specify a median filter width as an argument to add_recording( ). Five to ten minutes is typically a good width, but very noisy data may require an even wider window. Other basic filter types (e.g. mean or max) are simple to implement, as a general_filter( ) function is provided. This function does not use a filter width specified in number samples, but in time. This is important because beat-to-beat samples will not be uniformly spaced. FIG. 3 shows the result of applying a 10-minute median filter to a set of QTc annotations containing lots of outliers.

FIG. 3 depicts Filtering noisy annotations. This recording is from a 32-year-old female LQT1 patient in the THEW E-HOL-03-0480-013 database. Over 80,000 QTc values were annotated. Directly plotting these values produces the cyan line. Applying a median filter with a 10 minute window (i.e., passing filtering=10 to the add_recording( ) function) produces the blue line.

Subplots:

To display multiple plots in the same window or file, you can create an ECGFigure object and specify the number of rows and columns. Then, when creating an ECG Clock, you specify the "parent figure" and the clock's location on that figure. Single-plot figures also work this way, as a subplot inside a parent figure, but the parent figure is created automatically when you instantiate a clock without specifying a parent.

Annotations:

An add_annotation( ) function is available to add text labels and arrows to a plot. You must specify the location of the arrow head (time, radius) and tail (x, y location in the figure). A typical use for this function might be to identify the location of a maximum value, for example.

Case Studies

We will demonstrate by examples the utility of several plots from the perspectives of both clinicians and researchers.

QTc Vs. Age

Figure 4:
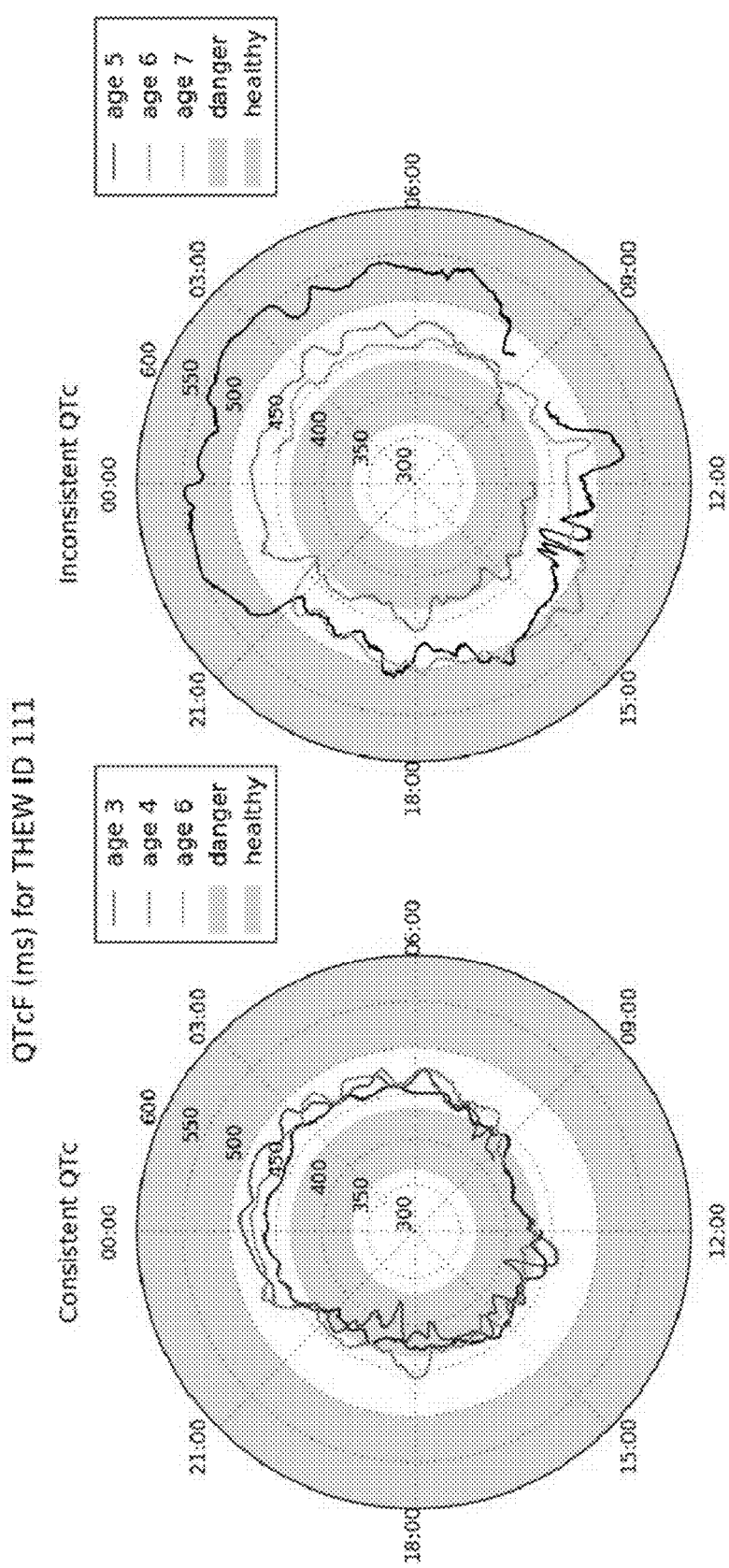
FIG. 4 is an example of ECG clocks that show $QT_cF$ evolution with age of the patient.

In FIG. 4, we show the same male LQT2 patient's QTc recorded at five different ages. On the left, we see that QTc is very stable when comparing ages 3, 4, and 6. At ages 5 and 7, though, his QTc has increased by over 50 msec, for much of the day; this is shown on the right, along with the age 6 plot for reference. This patient's QTc indicated relatively low risk in the recordings on the left (but with slight prolongation at night), yet it indicates high risk during the two "anomalous" recordings. Unfortunately, we do not have information about prescriptions or other possible causes for the prolongation at ages 5 and 7, but his physician would immediately investigate the cause of these deviations from the baseline—potentially drug interactions or hormonal changes—when presented with the plot. Finally, note the distinct "LQT2-like" shape of the plots, where QTc increases at night (similar to the patient in FIG. 1). This asymmetry could aid in diagnosis, preempting genetic testing in some cases. Note that we have chosen to augment the plots with static ranges for "healthy" and "dangerous" QTc values.

Drug Trial

Figure 5:
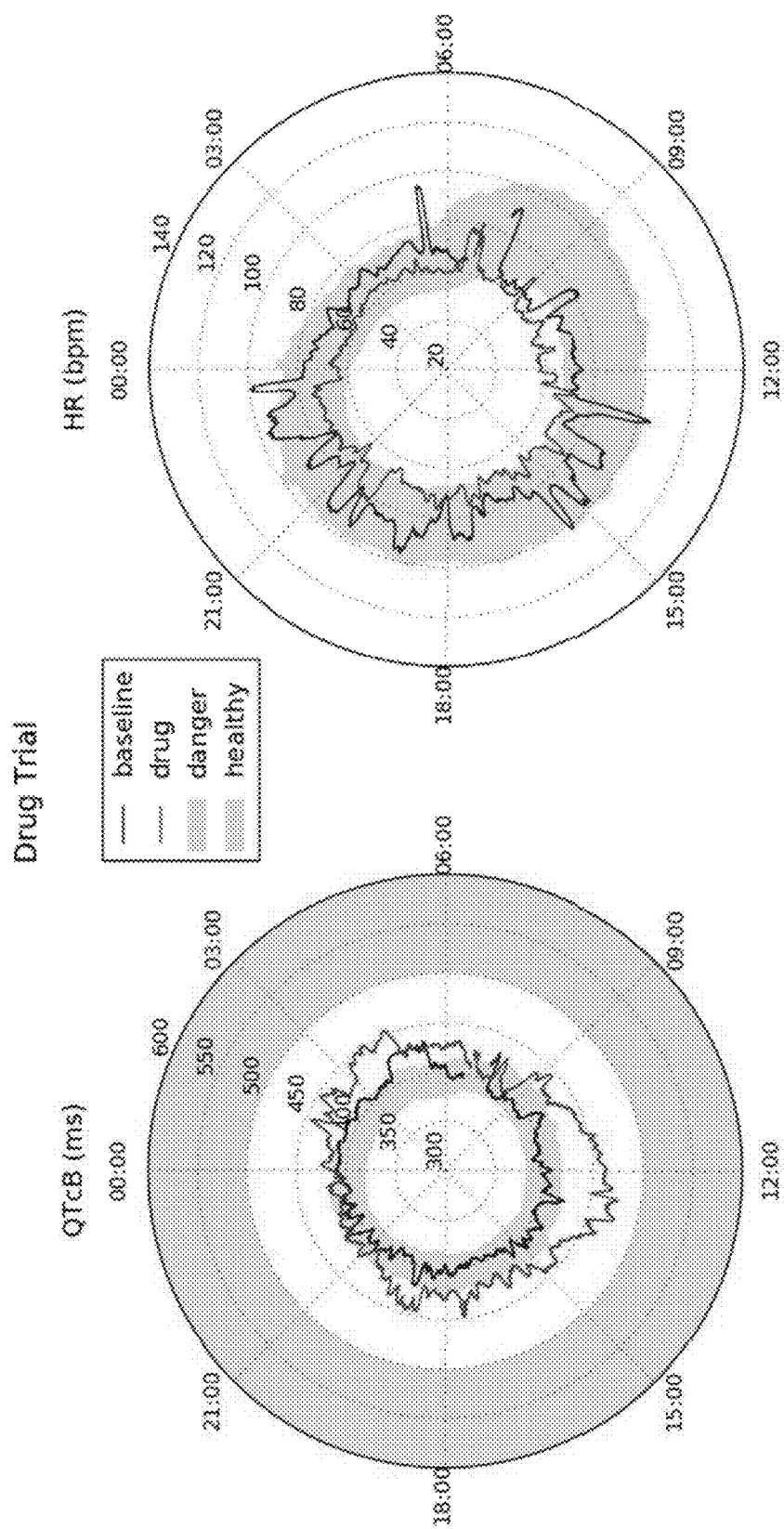
FIG. 5 shows ECG clocks depicting the effects of sotalol (a beta blocker/antiarrhythmic drug) on a healthy patient.

Another typical use of plotting multiple Holter readings on the same axes is shown in FIG. 5, where we compare a patient's baseline QTc and heart rate to his QTc and heart rate on an antiarrhythmic drug. The drug was administered in the morning, and we can see its effect on QTc increase into the afternoon, drop off until roughly midnight, and then re-emerge during sleep. The effect on heart rate is more immediate and consistent throughout the day. This presentation may encourage the drug manufacturer to perform longer-duration monitoring, and/or help to characterize the drug's typical impact.

FIG. 5 depicts the effects of sotalol (a beta blocker/antiarrhythmic drug) on a healthy subject. Green ranges are defined by the inner 68 percentile in healthy male patients, i.e., approximately equivalent to plus/minus one standard deviation. The patient's heart rate is lower and less variable on the drug, and their QTc is much higher—both known effects of sotalol. A cardiologist would be able to use similar plots for their patients to determine if prescriptions were working as expected, and also to monitor medication adherence.

For the heart rate plot, we use the generic ECGClock class and simply modify the default axis range to 20-140. The green range for heart rate should perhaps be viewed as "normal" rather than "healthy"; it represents the typical range of values for the healthy population, but values outside of that range could be due to exercise, for example. Some patients may have drastically different sleep schedules than the average person. e.g. due to working third shift. In the figure, we notice that this patient's heart rate pattern appears to be misaligned by a couple of hours compared to the "normal" range. In cases like this, it may be desirable to rotate the "expected" range to match the patient's schedule. We will be adding an offset parameter to the library to allow this. (This will also be useful to adjust annotation data containing incorrect timing information.)

Comparing Genotypes

Figure 6:
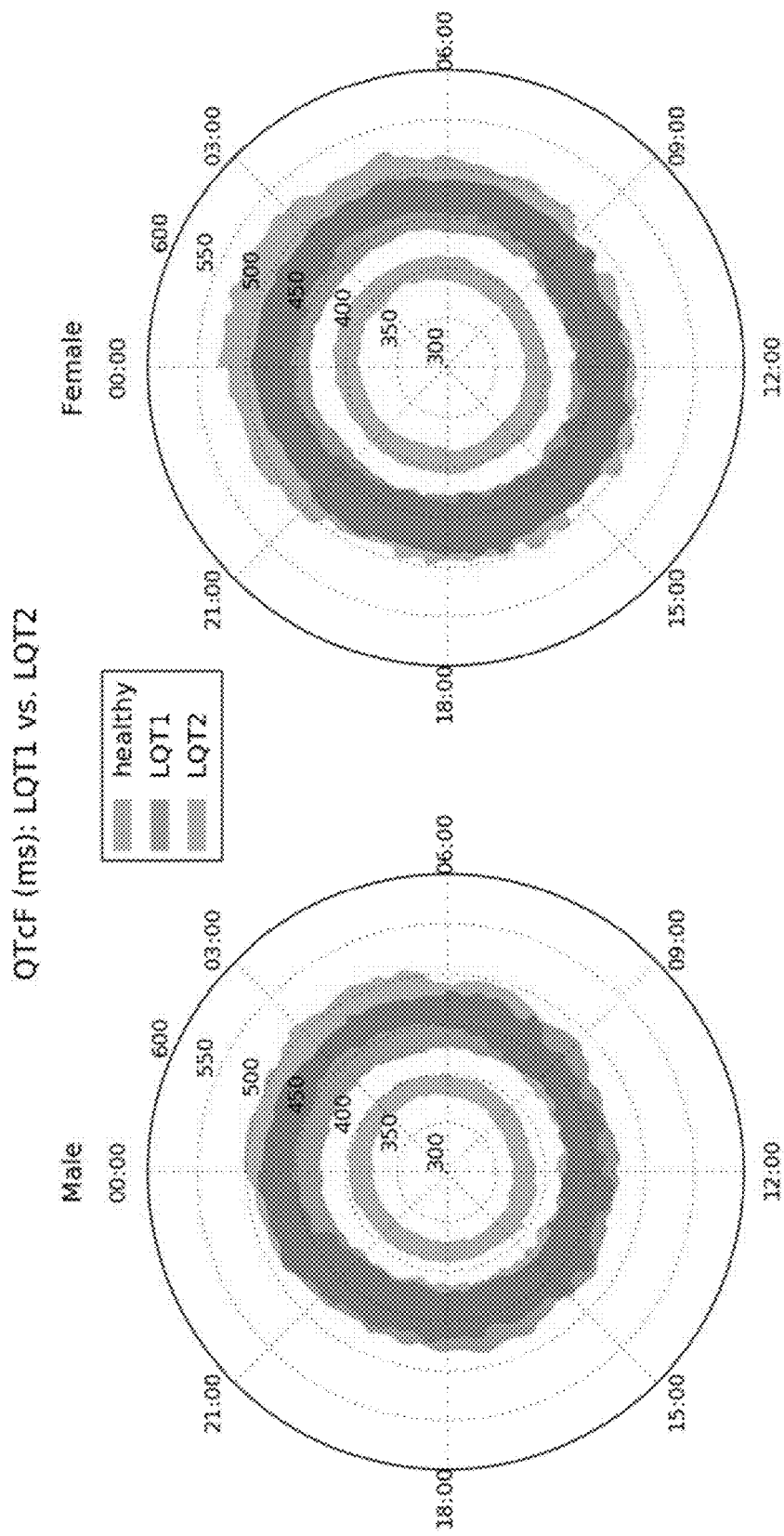
FIG. 6 shows ECG clocks comparing two groups (to a healthy group)

So far we have looked mostly at individual Holter recordings. The ability to compare groups of recordings is also very useful, though. For example, in a drug trial, we may want to compare a large group of baseline Holters to a group of "on drug" Holters. An example where we compare two groups of patients is given in FIG. 6. In this figure, we look at the interquartile range (IQR) of QTc in patients with LQT1 and LQT2, with healthy patients also shown for reference. We can clearly see that QTc prolongation only increases at night in the LQT2 group; in LQT1, it is quite stable, and almost indistinguishable from LQT2 during the day. Additionally, most LQT1 patients never enter the "danger" area, whereas LQT2 patients—particularly females—have a relatively high chance of reaching dangerous prolongation levels during sleep. This type of plot tells a much more complete story than a list of basic statistics from the recordings.

To generate the data for this plot, we annotated the QT and RR intervals in all healthy, LQT1, and LQT2 Holters from the THEW database, used this information to compute QTc at every heart beat, and finally computed the percentiles for all beats in each 1-minute window. The resulting values are stored in the CSV files described herein.

Heart Rate Dipping

Figure 7:
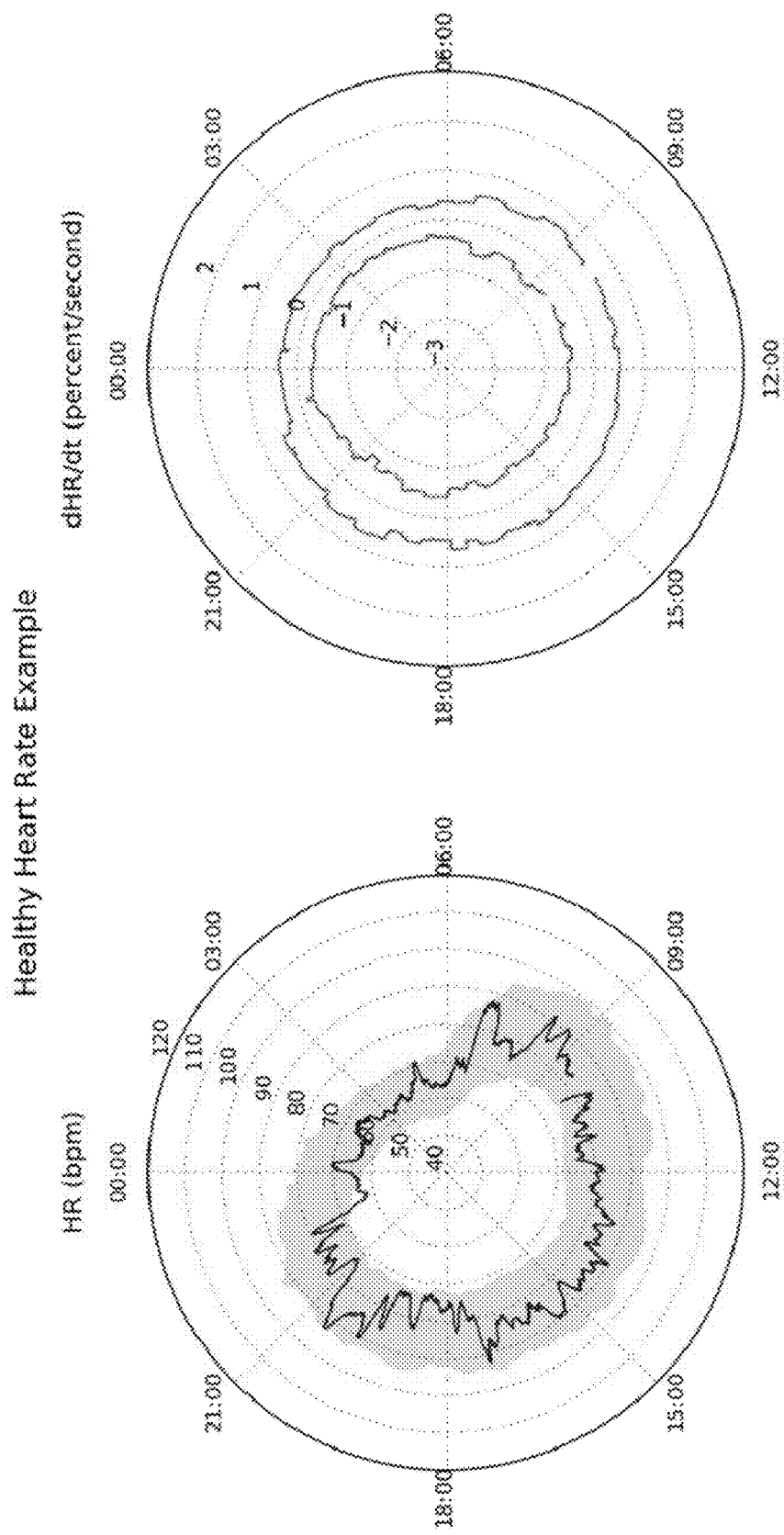
FIG. 7 depicts ECG clocks showing heart rates and derivative of heart rate (upper and lower bounds) for a healthy patient.

FIG. 7 depicts heart rate and time derivative of heart rate for a healthy subject. The plot on the left provides the doctor with a comprehensive picture of the patient's heart rate and HRV. This particular patient's heart rate drops from ~80 bpm during the day to ~65 bpm at night, and appears to fluctuate across a range of ~10 bpm throughout the day. The green region indicates the interquartile range for heart rate in healthy subjects. The red lines on the right represent the upper and lower bounds for rate of change, dHR/dt, normalized to percentage change rather than beats per minute (bpm) change. This shows how fast the patient's heart rate is able to change, and is an example of how the ECG Clock library can be easily extended to display unconventional features.

In addition to the range of heart rate (HR), we may also be interested in its rate of change. The HRDerivClock class was created as an example of how the ECG Clock can be extended to view other features. In this class, we redefine the default axis range, and apply a derivative( ) function to the heart rate data as it is loaded. We can then plot either the derivative at each data point, or its upper and lower bounds within a sliding window. On the right side of FIG. 7, we show the upper and lower bounds. These bounds tend to stay at around +/−0.5 percent/second, meaning that a change from 80 to 65 bpm (about 20%) would take at least 40 seconds. We further note that changes take place more slowly at night. A very narrow range on this plot may indicate that the patient has trouble adapting their heart rate to different situations.

ECG clocks can be very useful for diagnosis, treatment, and monitoring of the Long QT Syndrome. They are also instructive in research involving both the congenital and drug-induced forms of this disease. Likewise, we have seen that heart rate clocks can be used for monitoring heart rate variability and drug response. Other embodiments of the present invention are applicable to other cardiac features, such as, for example, PR interval (the time from the beginning of the P wave until the beginning of the QRS complex).

The highlighted regions in the ECG clocks depicted herein can assist a physician in decision making, but the annotation data could also be used as input to a more advanced decision support system, providing the doctor with not only the picture, but recommendations.

ECG tracings are typically always presented at the same scale—10 mm/mV, and 25 mm/s—allowing clinicians and researchers to develop their tuition about Normal vs. abnormal tracings. Axes ranges for ECG clocks should be standardized for the same reason. For QTc, we have found that 300 ms-600 ms is usually a good plot range, but in extreme cases it must be extended up to 700 ms.

In some embodiments of the present invention, a web interface is provided so that non-programmers can simply upload data or annotations and generate clocks. Additionally, example IPython notebooks will simplify the process for programmers who prefer that environment.

Figure 8:
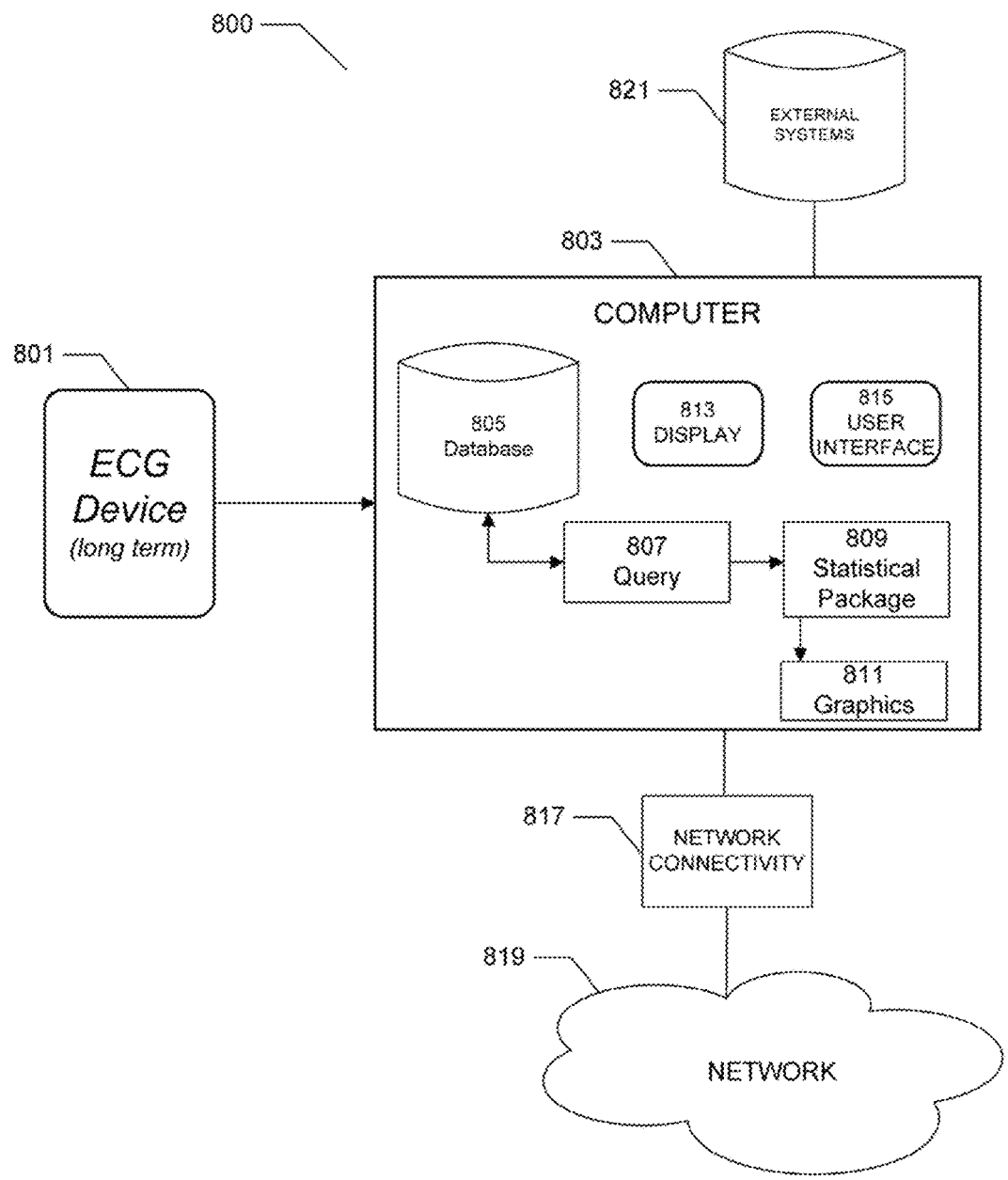
FIG. 8 depicts a functional block diagram of a typical system of the present invention.

FIG. 8 depicts a functional block diagram of a typical system of the present invention. The device of the present invention includes the ECG clock diagnostic device having a variable length radial hand and a circular face that may be represented on a display such as a computer display, or may include the components to construct the ECG clock diagnostic device such as display components, printers, or the like. The ECG clock may also be part of a larger system, such as that depicted in FIG. 8 that may include external systems, network elements and network components and systems, and the like. As will become evident, the components depicted may be substituted for others, eliminated, or added to with other components. The system 800 comprises a computer 803 having various functional elements as depicted in FIG. 8. An electrocardiogram device 801 capable of long term ECG data collection can be seen operatively connected to the computer 803. An electrocardiogram data receiver module, software element or component may reside on the computer 803 or components of the computer 803 to facilitate transfer of electrocardiogram data from the ECG device 801 to the computer 803. Such electrocardiogram data receiver module may also reside in an external system or component of a system and be connected to the computer 803 by way of a network connection, a physical connection, a wireless connection, or the like. The ECG device 801 may be, for example, a Holter monitor. ECG and related data from the ECG device 801 is then transferred or otherwise sent to the computer 803 and retained in a database 805 or the like. A database may include, for example, flat files as well as more sophisticated relational schemes. A query function 807 accesses the necessary data from the database 805 and incorporates the data into a statistical package 809 that creates the necessary information to construct an ECG clock or clocks with parameters that have been specified by the user, a computer program, or the like. Graphics software 811 in turn constructs the visual ECG clock and related forms, colors and annotations, as depicted herein. The ECG clock is in turn physically embodied in a display 813. A user interface 815 allows interaction between a user and the various components of the computer 803. The ECG clock and related information can be accessed through network connectivity 817 and a network 819 such as the internet. Security may be incorporated as necessary. Further, external systems 821 may access the ECG clock(s) and related information, and may also, in some embodiments of the present invention, provide additional information that may be used with the ECG clocks of the system 800.

It is, therefore, apparent that there has been provided, in accordance with the various objects of the present invention, an ECG clock electrocardiogram based diagnostic device and method.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, claims and drawings appended herein.

What is claimed is:

1. An ECG clock electrocardiogram based diagnostic device comprising:
   a computer having a processor, memory, and access to computer readable media;
   an electrocardiogram data receiver module residing on the computer and configured to receive electrocardiogram data wherein the electrocardiogram data comprises electrocardiogram variables and time of day values associated with each electrocardiogram variable value;
   a computer program stored on the computer readable media where the computer program executes the steps of:
   retrieving the electrocardiogram data received by the electrocardiogram data receiver module;
   creating on a computer display an ECG clock comprising a variable length radial hand and a circular face wherein a complete 360 degree rotation of the variable length radial hand correlates to a diagnostic time interval and wherein the length of the radial hand at a given angular position on the circular face correlates to an electrocardiogram variable value that is unique to the time of day or time value associated with that angular position; and
   applying the retrieved electrocardiogram data to the displayed electrocardiogram clock such that a patient specific geometric pattern of the retrieved electrocardiogram data is displayed on the computer display for ease of diagnostic inspection by a medical practitioner or clinician.

2. The ECG clock electrocardiogram based diagnostic device of claim 1, wherein the electrocardiogram data is sourced from a Holter monitor.

3. The ECO clock electrocardiogram based diagnostic device of claim 1, wherein the electrocardiogram data is sourced from an electrocardiogram recording database.

4. The ECG clock electrocardiogram based diagnostic device of claim 1, wherein the electrocardiogram variable value is heart rate.

5. The ECG clock electrocardiogram based diagnostic device of claim 1, wherein the electrocardiogram variable value is $QT_c$ interval.

6. The ECG clock electrocardiogram based diagnostic device of claim 1, wherein the diagnostic time interval is one day.

7. The ECG clock electrocardiogram based diagnostic device of claim 1, wherein the displayed ECG clock further comprises color bands representative of safe and unsafe electrocardiogram variable value parameters.

8. The ECG clock electrocardiogram based diagnostic device of claim 1, wherein the displayed ECG clock further comprises electrocardiogram variable values from a larger population for comparison of the patient specific geometric patterns to geometric patterns of the larger population.

9. The ECO clock electrocardiogram based diagnostic device of claim 1, further comprising a data filter stored on computer readable media for filtering noisy electrocardiogram variable values.

10. The ECG clock electrocardiogram based diagnostic device of claim 1, wherein the displayed ECG clock further comprises multiple patient specific geometric patterns.

11. The ECG clock electrocardiogram based diagnostic device of claim 10, wherein the multiple patient specific geometric patterns correlate to patient age.

12. The ECG clock electrocardiogram based diagnostic device of claim 1, wherein the computer display is selected from the group consisting of a flat panel display, a smart phone display, a tablet display, and a watch display.

13. An electrocardiogram clock stored on computer readable media and graphically displayed on a computer monitor comprising a variable length radial hand and a circular face wherein a complete 360 degree rotation of the variable length radial hand correlates to a diagnostic time interval and wherein the length of the radial hand at a given angular position on the circular face correlates to an electrocardiogram variable value that is unique to the time of day or time value associated with that angular position;

and wherein the displayed electrocardiogram clock displays a plurality of retrieved electrocardiogram variable values that are unique to a time of day or time value associated with the angular position on the electrocardiogram clock such that a geometric pattern of the retrieved electrocardiogram variable values is displayed on the computer display for ease of diagnostic inspection by a medical practitioner or clinician.

14. The electrocardiogram clock of claim 13, wherein the electrocardiogram variable value is heart rate.

15. The electrocardiogram clock of claim 13, wherein the electrocardiogram variable value is $QT_c$ interval.

16. The electrocardiogram clock of claim 13, wherein the diagnostic time interval is one day.

17. The electrocardiogram clock of claim 13 further comprising color bands representative of safe and unsafe electrocardiogram variable value parameters.

18. The electrocardiogram clock of claim 13, wherein the electrocardiogram clock comprises a plurality of two dimensional electrocardiogram clocks stacked to form a three dimensional representation graphically displayed on a computer monitor.

19. A method for diagnosing heart related anomalies, the method comprising the steps of:
retrieving on a computer electrocardiogram data;
creating on a computer display an ECG clock comprising a variable length radial hand and a circular face wherein a complete 360 degree rotation of the variable length radial hand correlates to a diagnostic time interval and wherein the length of the radial hand at a given angular position on the circular face correlates to an electrocardiogram variable value that is unique to the time of day or time value associated with that angular position; and
applying the retrieved electrocardiogram data to the displayed electrocardiogram clock such that a geometric pattern of the retrieved electrocardiogram data is displayed on the computer display for ease of diagnostic inspection by a medical practitioner or clinician.

20. The method for diagnosing heart related anomalies of claim 19, further comprising the step of filtering on a computer the retrieved electrocardiogram data prior to applying the retrieved electrocardiogram data to the displayed electrocardiogram clock.

* * * * *

UNITED STATES PATENT AND TRADEMARK OFFICE
CERTIFICATE OF CORRECTION

PATENT NO. : 10,085,667 B2
APPLICATION NO. : 15/368587
DATED : October 2, 2018
INVENTOR(S) : Jean-Philippe Yves Couderc et al.

Page 1 of 1

It is certified that error appears in the above-identified patent and that said Letters Patent is hereby corrected as shown below:

In the Claims

Column 13, Line 8, Claim 3, 'The ECO clock' should read -The ECG clock-

Column 13, Line 29, Claim 9, 'The ECO clock' should read -The ECG clock-

Signed and Sealed this
Nineteenth Day of March, 2019

Andrei Iancu
*Director of the United States Patent and Trademark Office*